(12) United States Patent
Kramer

(10) Patent No.: US 6,497,672 B2
(45) Date of Patent: Dec. 24, 2002

(54) DEVICE AND METHOD FOR MEASURING THE POSITION OF ANIMATE LINKS

(75) Inventor: James F. Kramer, Menlo Park, CA (US)

(73) Assignee: Virtual Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/565,730

(22) Filed: May 5, 2000

(65) Prior Publication Data

US 2001/0020140 A1 Sep. 6, 2001

Related U.S. Application Data

(62) Division of application No. 08/957,696, filed on Oct. 24, 1997, now Pat. No. 6,110,130.

(51) Int. Cl.$^7$ .............................................. A61B 5/103
(52) U.S. Cl. ..................................................... 600/595
(58) Field of Search .................................. 600/587, 595

(56) References Cited

U.S. PATENT DOCUMENTS

| | | | |
|---|---|---|---|
| 4,108,164 A | 8/1978 | Hall, Sr. | |
| 4,270,050 A | 5/1981 | Brogardh | 250/231 R |
| 4,302,138 A | 11/1981 | Zarudiansky | |
| 4,414,537 A | 11/1983 | Grimes | 340/365 R |
| 4,444,205 A | 4/1984 | Jackson | 128/782 |
| 4,542,291 A | 9/1985 | Zimmerman | 250/231 R |
| 4,575,297 A | 3/1986 | Richter | |
| 4,715,235 A | 12/1987 | Fukui et al. | 73/862.68 |
| 4,937,444 A | 6/1990 | Zimmerman | 250/231.1 |
| 4,986,280 A | 1/1991 | Marcus et al. | 128/774 |
| 5,047,952 A | 9/1991 | Kramer et al. | 364/513.5 |
| 5,086,785 A | 2/1992 | Gentile et al. | 128/782 |
| 5,143,505 A | 9/1992 | Burdea et al. | |
| 5,184,009 A | 2/1993 | Wright et al. | 250/227.11 |
| 5,184,319 A | 2/1993 | Kramer | 364/806 |
| 5,280,265 A | 1/1994 | Kramer et al. | 338/210 |
| 5,316,017 A | 5/1994 | Edwards et al. | 128/782 |
| 5,451,924 A | 9/1995 | Massimino et al. | 340/407.1 |
| 5,482,056 A | 1/1996 | Kramer | |
| 5,587,937 A | 12/1996 | Massie et al. | |
| 5,619,180 A | 4/1997 | Massimino et al. | 340/407.1 |
| 5,631,861 A | 5/1997 | Kramer | 364/406 |
| 5,676,157 A | 10/1997 | Kramer | |
| 5,912,658 A | 6/1999 | Bergamasco et al. | |

FOREIGN PATENT DOCUMENTS

WO      WO94/01042      1/1994

OTHER PUBLICATIONS

Shahinpoor, M., "A new effect in ionic polymeric gels: the ionic flexogelectric effect," *Proceedings of the SPIE —The International Society for Optical Engineering* (1995) vol. 2441, pp. 42–53.

Weiss, Jonathan D., "A Gallium Arsenide strain–optic voltage monitor," *Sensors* (Oct. 1995), pp. 37–40.

*Primary Examiner*—Kevin Shaver
*Assistant Examiner*—Pamela Wingood
(74) *Attorney, Agent, or Firm*—Paul M. Thyfault

(57) ABSTRACT

An exoskeleton device is provided for measuring positions of links and angles of joints of an animate body, where the body comprises a plurality of links joined by intervening joints. The device is affixed at a first mobile terminus of said animate body and a second fixed terminus, having device links displaced from animate links, where the device links are connected by device joints and having sensor means for measuring the angle of the device joints. Using the signals from the sensor means, one can determine the position of the terminal device link and based on knowledge of the animate body structure, calculate the animate angle joints.

36 Claims, 13 Drawing Sheets

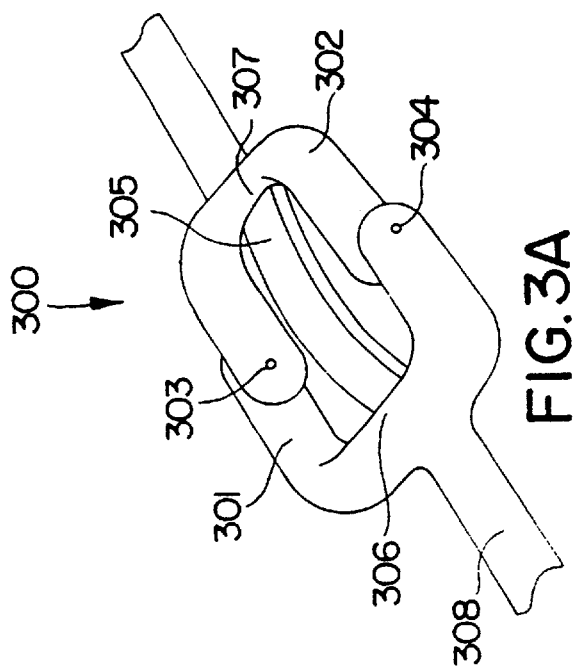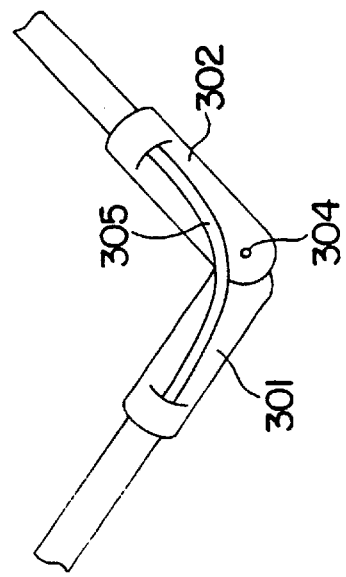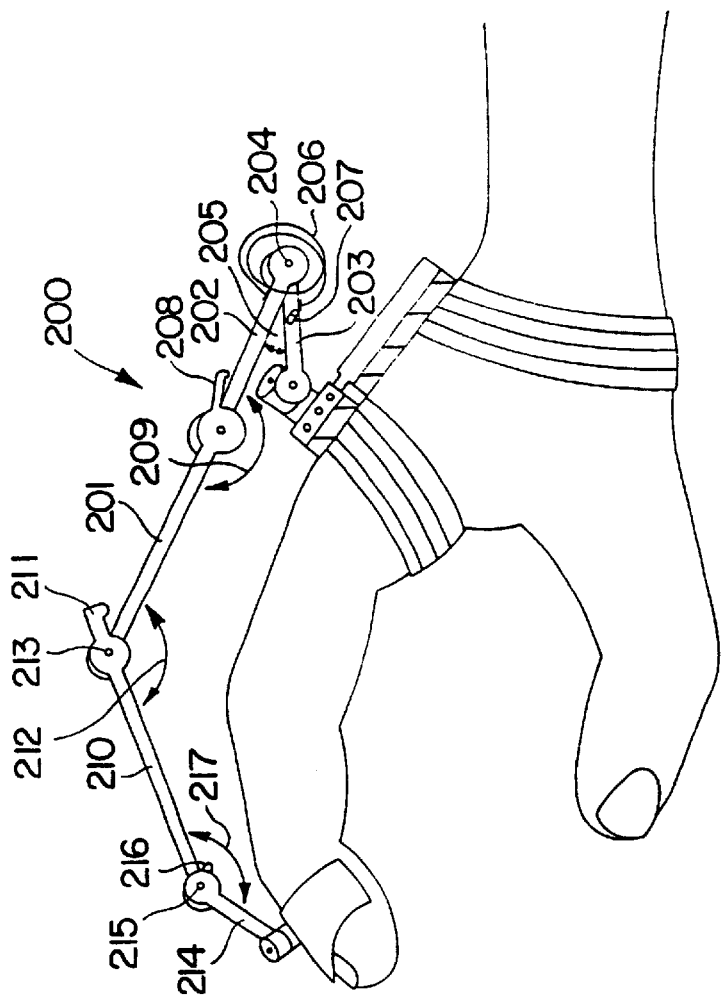

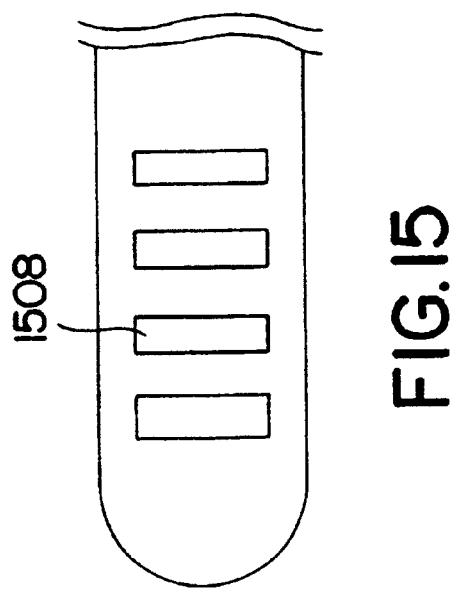
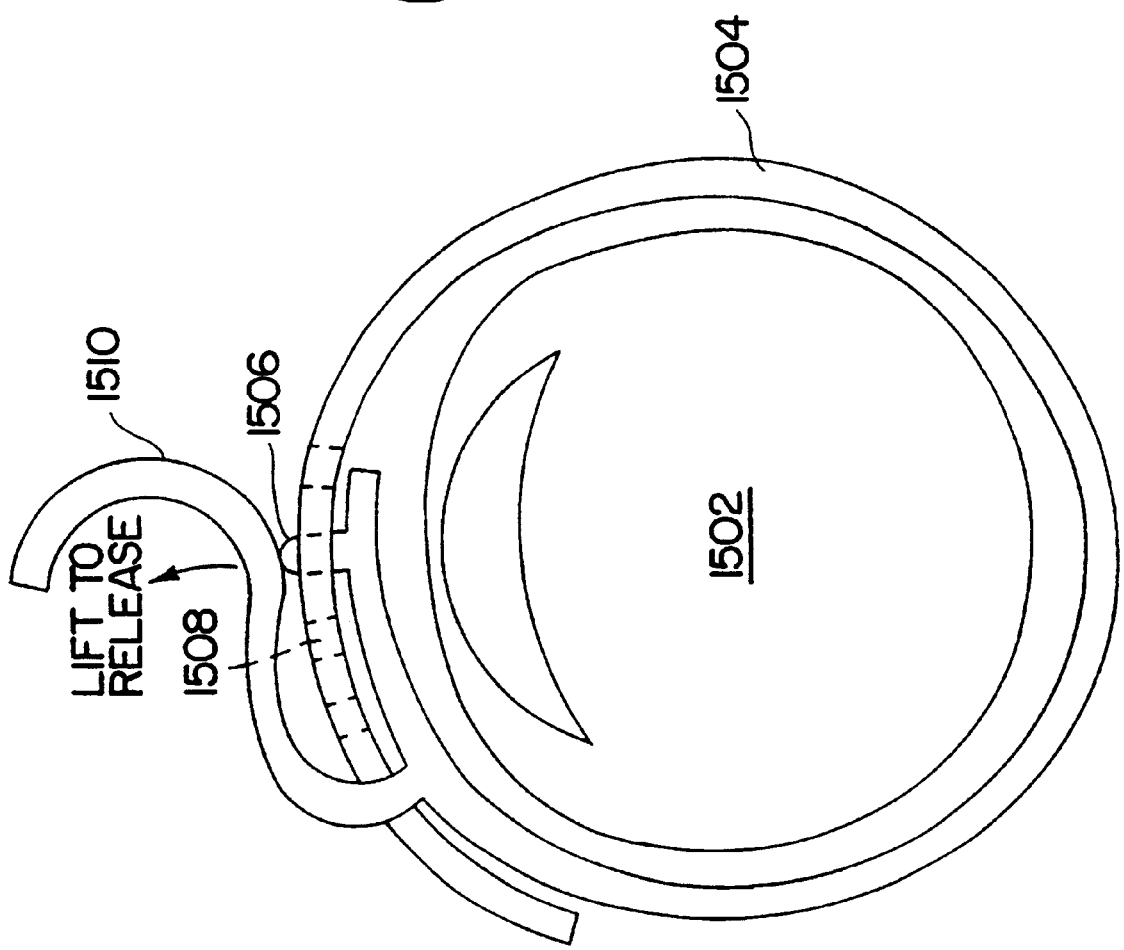
FIG.15

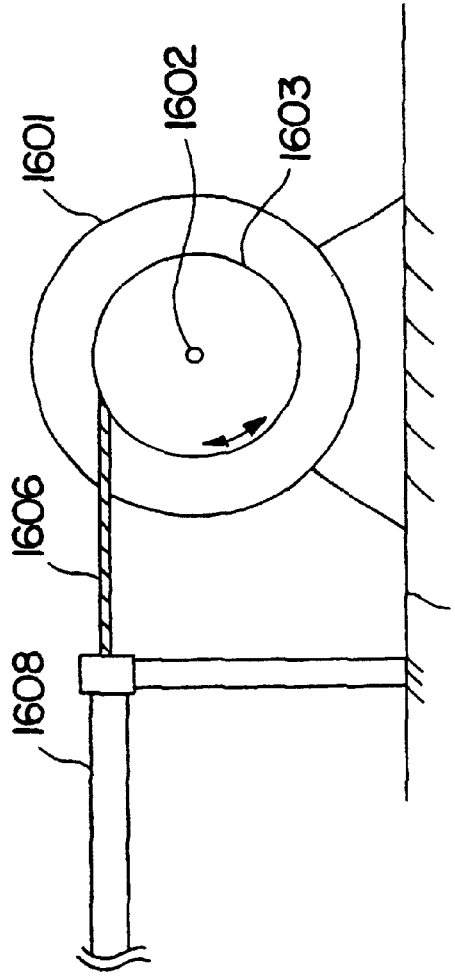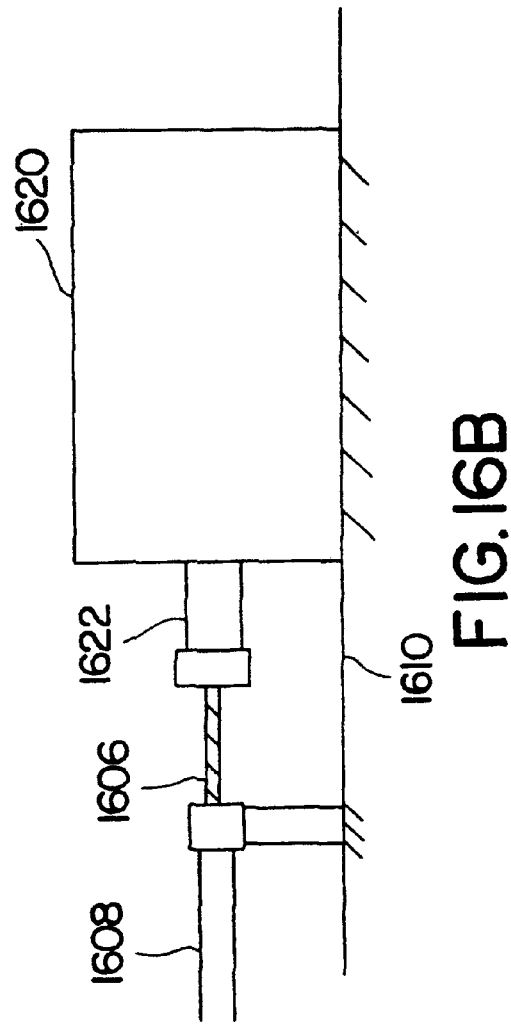
FIG.16A
FIG.16B

DEVICE AND METHOD FOR MEASURING THE POSITION OF ANIMATE LINKS

This is a division of application Ser. No. 08/957,696 now U.S. Pat. No. 6,100,130, filed Oct. 24, 1997.

BACKGROUND OF THE INVENTION

There has been an increasing interest in the ability to measure position of the fingers and hand in such areas as virtual reality, telerobotics, graphical animation and medical hand function assessment. There have been a number of hand-measurement devices constructed to date for measuring the position of the fingers; however, each such finger-measuring device has a common inadequacy, among various other shortcomings. The primary inadequacy of the devices being that they measure joint angles of the hand and then rely upon a mathematical model of the physical hand and "forward kinematic" mathematical calculations to produce an estimate of fingertip positions. Measuring finger joint angles explicitly is satisfactory when the goal of the device is to be used for measuring joint angles. However, in many of the aforementioned fields of study, the desired parameter to be measured is the position of the fingertip. When the position of the fingertip is desired, by measuring the finger joint angles and combining these angles with the mathematical model of the hand, errors in both the joint angle measurements and the model add to produce a cumulative error in fingertip position.

One common source of error is introduced by employing a simplified mathematical model of the hand, where each joint is approximated as a revolute joint with a fixed axis of rotation. More realistically, the instantaneous joint axis of a finger actually varies as a function of the joint angle. Additionally, measuring the joint angles of the finger often requires that a goniometer be affixed to phalanges comprising the links by the joint. Any unmeasured relative motion between these affixation points and the phalanges introduces error in the joint measurement. Hence, the number of such unmeasured affixation points is preferably kept to a minimum.

Devices which illustrate the above deficiencies are exemplified by the gloves described in U.S. Pat. Nos. 4,542,291, 4,937,444, 5,047,952, 5,280,265, 4,986,280, 5,086,785, 4,414,537, 5,184,009, 4,444,205, 5,316,017, 4,715,235.

SUMMARY OF THE INVENTION

Methods and devices are provided for accurately determining the positions of animate links and angles of animate joints of an animate kinematic chain of an animate body. The animate body comprises a plurality of animate links interconnected by animate joints to provide the animate kinematic chain. The device comprises a plurality of rigid device links interconnected by fixed-axis revolute device joints to provide a device kinematic chain. Two of the device kinematic chain links are terminal device links, each held in known rigid relationship to an animate link, designated as the terminal animate links, via attachment means. At least one of the device joints is displaced away from the animate links. There are at least three device joints with two sensing device joints on opposing ends of a device link. The sensing device joints provide for measurement of device joint angles. The number of sensing device joints is at least sufficient to determine the relative placement of the two terminal device links. The angle of each of said sensing device joints is measured and transmitted as a signal to a signal processor. The signal processor determines the relative placement of the terminal device links using said signals and using forward kinematic mathematical techniques on the device kinematic chain. Further, employing knowledge of the placement of the terminal device links relative to the terminal animate links, the signal processor can calculate the relative placement of the terminal animate links. By using the relative placement of the terminal animate links, and a kinematic model of the animate body, which includes modeled animate links and animate joints, the positions of such animate links and the angles of such animate joints can be calculated using inverse kinematic mathematical techniques. The subject invention finds particular application with the hand.

BRIEF DESCRIPTION OF THE DRAWINGS

FIG. 2 is a side view of a hand wearing a second embodiment of the device.

FIGS. 3A–3I provide side and top views of various sensing device joints employing a variable-resistance strain-sensing goniometer and pivoting hinges.

FIG. 15 is an end view of a fingertip with an exemplary embodiment of a fastening strap for fastening the link chain of the fingertip.

FIG. 16A shows the end view of a rotary motor having a pulley which winds the tendon to generate tension relative to the associated sheath.

FIG. 16B shows the side view of a linear actuator with the tendon affixed to the actuator's moving element.

DESCRIPTION OF THE SPECIFIC EMBODIMENTS

Figures 1A, 1B:
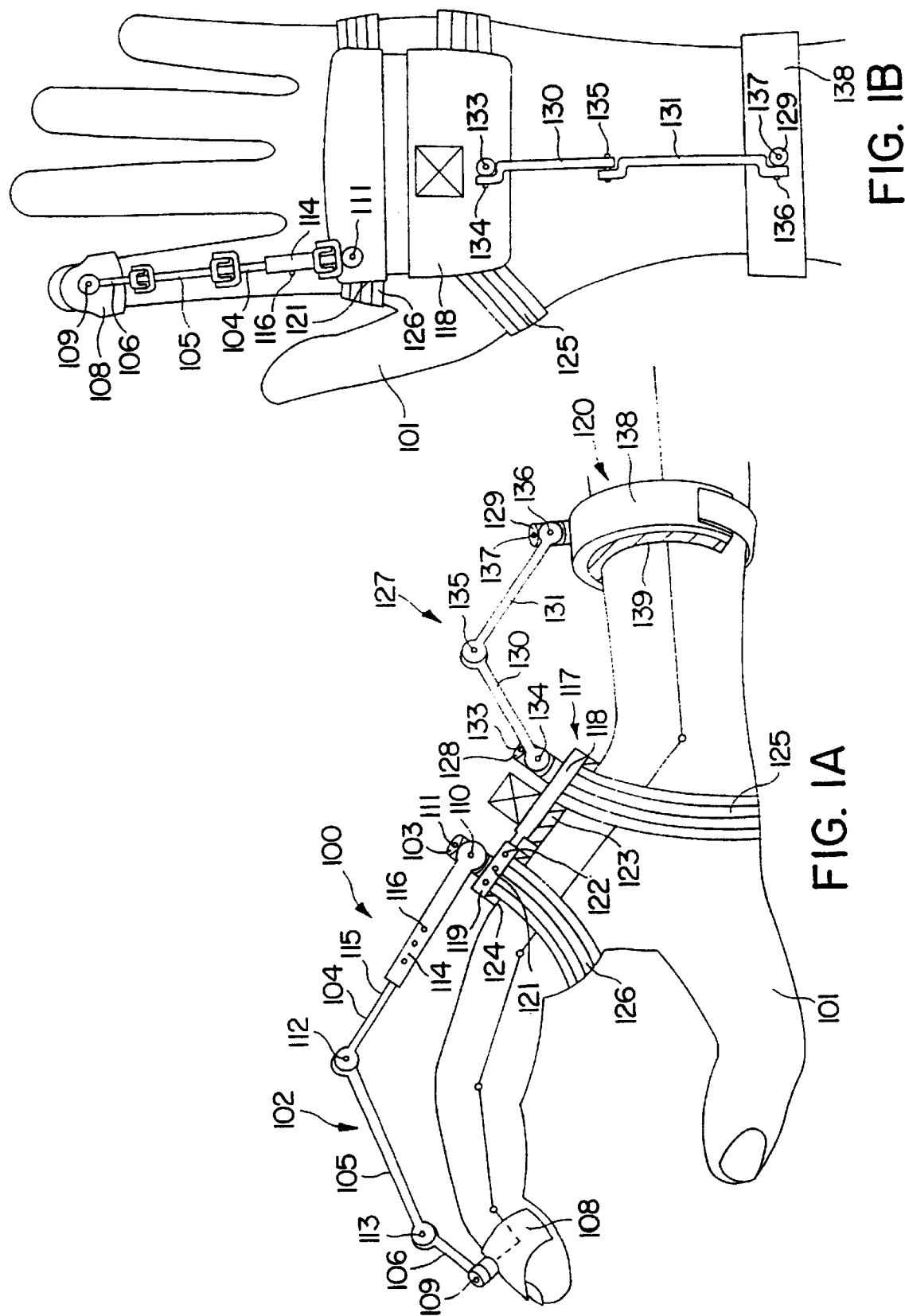
FIGS. 1A and 1B are side and top views, respectively, of a hand wearing a first embodiment of the device.

Devices are provided for measuring a first portion of an animate body in relation to a second portion of the animate body distal from the first portion. The animate body is best exemplified by the hand, although portions of other animate bodies are also capable of being measured. The first and second portions of the animate body are modeled by animate links and animate revolute joints, there being at least two animate links and at least one animate revolute joint. Having determined the position of the first portion of an animate body relative to the second portion of the animate body, inverse kinematics may be employed to determine the joint angles between the animate links of the animate body comprising the first and second portions.

The device comprises a plurality of rigid device links, which include two terminal device links and at lest one intermediate device link. One end of each of the terminal device links is mounted onto each of the first and second portions of the animate body, respectively, being affixed using a convenient attachment means. For example, in the case of the hand, one end of a first terminal device link is mounted onto the distal phalanx, and one end of a second terminal device link is mounted onto the dorsal side of the metacarpus. The links may be rods, tubes and the like, where the cross-sections widely vary, being circular, rectangular, triangular, I-shaped, arc-shaped, polygonal, "+"-shaped cross-sections and the like. The particular choice of shape and size will be determined by the desired design and will be dependent upon the nature of the material employed, required structural rigidity, size, weight, aesthetics, ease of manufacturer, use as a conduit, or the like. The number of links and interconnecting joints, as well as their kinematic structure may vary to accommodate for varying hand sizes, while maintaining a desirably low profile. Also, the device links may be telescopic to allow for changes in the length of the device link in relation to varying animate body sizes.

In many applications, there will be as few as four links and three device joints with two or more sensing device joints, with two sensing device joints on opposing ends of a link. However, more often there will be at least four device joints and at least five links.

The links and joints form a device kinematic chain. The device may have a single or plurality of device kinematic chains for measuring one or more animate kinematic chains, where two or more device kinematic chains may share a terminal link. Various attaching devices may be employed for affixing terminal device links to terminal animate links of the animate kinematic chain. The measurements derived by the device are not particularly sensitive to where the attaching device is affixed to the animate link.

Usually, for a device link joining parallel device joint axes, the cross-section will be relatively small relative to the length of the device link, i.e. the aspect ratio of the device link is much greater than one. A typical device link is normally 1–10 mm in the largest cross-sectional dimension. Normally, the device link, and the associated joint and device for measuring joint angle, will have a smaller cross-section than the animate body part with which it is associated.

When the animate body links are the phalanges of a hand, device links articulated similarly to the animate links may be placed on the dorsal side of each finger of the hand without mutual interference between the device links and the animate links. Typically, device links are placed about the animate body such that the animate links tends to articulate away from the device links; however, this need not always be the case. Note that if a device link were placed at the side of a finger, it would interfere with other fingers and other device links placed at the side of another finger. The fingers would then not be able to come together. A device link comprising a goniometer, for placing on the side of the index or pinkie metacarpophalangeal joint, could not be placed similarly on the side of the middle and ring fingers, due to the existence of the neighboring fingers.

The particular material which is employed for the device links and joints is not critical and may be metal, plastic, ceramic, composite, graphite, fiberglass, carbon-fiber or fiber-reinforced material, combinations thereof and the like.

The ends of the intermediate device links are connected by joints to other intermediate device links or terminal device links. The functionality of a revolute joint can be obtained by pinned joints, flexures and the like. The functional equivalent of a pinned joint may be achieved by a variety of articulated structures. One structure has a yoke at the end of one device link, with the end of the other device link extending into the yoke. Another structure has yokes at the end of each of the device links, where the arms of the yokes overlap. A third structure has the complementary ends of the device links flattened and abutting. Other structures may also find use, as convenient. For pinned joints, the pin can extend through the overlapping portion of the device links. Alternatively, instead of a pin, one device link may have a protuberance, where the other device link has a complementary concavity. Other means for allowing rotation between the two device links may also be employed. For flexures, one may form as a single body two device links with a thinner joining portion to create a region or point of articulation, referred to as a "live hinge." Similarly, two device links may be adjoined with a flexible sheet to allow for articulation between the two device links. Other articulation means may be employed, as convenient.

Means for measuring the angle of each of the joints is provided. The angle measuring means may vary with the nature of the joint and may include strain gages, Hall effect sensors, encoders, potentiometers, resolvers, optical goniometers, electromagnetic sensors, light fibers, resistive inks, piezo-resistive flex sensors, and the like. A preferred strain gage angle-measuring means is provided in U.S. Pat. Nos. 5,047,962 and 5,280,265. The various measuring devices may be mounted in functional relation to the joint to accurately provide a signal related to the angle defined by the two device links. For example, with a Hall effect goniometer, a magnetic element may be mounted to one device link and the Hall effect sensor mounted to the complementary link, such that the changes in angle of the joint produce a relative change in the flux lines of the magnetic field of the magnetic element as they are sensed by the Hall effect sensor. Thus, the signal detected by the Hall effect sensor is uniquely related to the joint angle.

Strain-sensing goniometers comprised of strain gages or other variable-resistance strain-sensing elements may find use with a variety of joints structures. The strain-sensing goniometers may be integral with the joint, mounted on the joint or placed at various sites in relation to the structural components of the joint. The strain-sensing goniometers may find use with hinges employing pins or protuberances, flexure hinges and the like.

For a flexure hinge, a strain-sensing goniometer may be incorporated into the flexure hinge or be associated with the flexure hinge. Various constructions can be devised for including strain-sensing goniometers with the flexure hinge. In one embodiment, the strain-sensing goniometer is molded into the flexure hinge with the neutral bend axis of the goniometer coinciding with the neutral bend axis of the hinge. The strain-sensing goniometer conveniently comprises dual or single piezo-resistance strain-sensing elements are described in U.S. Pat. Nos. 5,047,952 and 5,280,265, or a single piezo-resistance strain-sensing element as described in U.S. Pat. No. 5,086,785. When either of the aforementioned strain-sensing goniometers is employed, the flexure hinge should not adhere to the surface of the strain sensing element, but form a closely fitting channel for the strain-sensing element. In a second embodiment, one or more strain gage elements are molded into the flexure material of the flexure hinge, offset from the neutral axis and adhered to the flexure material. The strain gage elements are adhered to the flexure material so that strain is induced upon flexing of the flexure hinge.

In another embodiment, the strain-sensing goniometer may be rigidly affixed at its ends to the device links connected by the hinge, and bow away from the hinge between the rigid attached points. The strain-sensing goniometer may also reside in a cavity between the pivot points of a yoke-type hinge, where the ends of the goniometer are rigidly affixed to the links connected by the hinge. In such a case, the strain-sensing goniometer may pass directly through the hinge axis or lie on either side. When the strain-sensing goniometer does not lie along the central axes and pass through the central axis of the joint, the goniometer will bow during bending of the joint.

Strain-sensing goniometers may be constructed from a wide variety of strain-sensing materials, where selection of the specific material and construction is dependent upon manufacturability, durability, cost, signal strength, repeatability, noise, and the like. Typical strain-sensing materials include various piezo-resistive metal compositions (such as copper/nickel), piezo-resistive elastomers, piezo-electric gels, semiconductor strain gages, piezo-resistive links, and the like. Sensors employing substances producing other piezo-electric properties, such as piezo-voltaic, piezo-magnetic, and the like may be used. Piezo-electric gels which exhibit a "flexoelectric" effect are described in Shahinpoor, M., "A new effect in ionic polymeric gels: the ionic flexoelectric effect," *Proceedings of the SPIE—The International Society for Optical Engineering* (1995) vol. 2441, p. 42–53.

Strain-sensing goniometers may also be constructed using optical strain detection techniques. One such strain-sensing technique is based upon a fiber optic strain gage employing microbends as described in U.S. Pat. No. 5,132,529. Another optical strain-sensing techniques uses the strain-sensitive absorption properties of various substances as described in U.S. Pat. No. 4,270,050, and the paper by Jonathan D. Weiss, "A Gallium Arsenide strain-optic voltage monitor," *SENSORS*, pp. 37–40, October 1995. Another technique uses optical strain interferometry.

Goniometers may also be constructed using optical technology which are based on light loss due to bending, such as provided by U.S. Pat. Nos. 4,542,291, 4,937,444 and 5,184,009. Other optical goniometers may produce a signal indicative of bend angle as measured by the phase difference between the light beam passing along two neighboring fibers which are flexed.

Another device embodiment employs other goniometric devices, such as potentiometers, resolvers and encoders. The potentiometers, resolvers and encoders may be mounted in functional relation to the pin of a pinned-axis revolute joint, so that movement of the joint changes the resistance of the potentiometer, voltage of a resolver or the number of counts of an optical encoder.

The device may comprise various combinations of flexure device joints and abduction device joints. The device joints of interconnected device links need not all be parallel. When referring to the orientation of a joint, it is understood that the reference is to the axis of the joint. In the case where the animate body is the hand, the abduction device joints are typically orthogonal to the flexure device joints and orthogonal to the metacarpus, whereas the flexure device joints typically are nearly parallel to flexure animate joints. In one embodiment for a hand, where the position of a fingertip is to be measured, in one configuration of the device, where one end of the device is attached to the fingertip and the other end of the device is attached to the metacarpus near the metacarpophalangeal joint, when there is no abduction of the finger, the flexure device joints are parallel to the proximal and distal interphalangeal joints of the associated finger.

Depending upon the location of the portion of the animate body to which the device is mounted, various mounting structures may be employed. When the animate body is a finger, one end of the device may be affixed to a supporting entity, such as a fingertip clip, strap, elastic or inelastic band, thimble-like structure, or other structure which may also be adjustable to fit varying fingertip diameters. The mounting entity maintains the position of the end of the structure relative to the surface of the animate body. The other end of the device may be affixed to a supporting entity such as a rigid or semi-rigid plate, or flexible pad, where the plates, pads, etc., may conform to the back of the hand to varying degrees, and may be strapped to the hand or attached to a suitably reinforced glove. Other means of mounting the device to the back of the hand may also be employed.

As mentioned previously, the device measures the position of a first portion of an animate body relative to a second portion. The principle is that a well defined device structure will allow very precise determination of such relative positions. From the relative position information of the device, the joint angles between animate links of the associated animate body parts can be determined using inverse kinematic techniques. Such an inverse kinematic technique is described in PCT/US93/06408, with a specific example for determining the angle of finger tips. To use inverse kinematics, a link/joint model of the animate body is used. However, in typical situations, such a model is only an approximation of the true animate link length and animate joint axis positions. As such, the animate joint angles determination from the inverse kinematic calculations are only approximations of the true animate joint angles. In certain applications, such as grasping in a virtual reality, where the animate body is a hand, the true joint angles of the animate joints are less important than the true position of the fingertips of the hand.

Since we are using a well characterized device for measuring the fingertip position, we are measuring the critical element directly and accurately. The antimate joint angles, i.e. finger joints, need primarily be determined for graphical display purposes and minor errors in their determination will not significantly affect the ability of a person to reliably grasp and manipulate a virtual object. In contrast, previous approaches in the art have measured the animate joint angles directly and then used forward kinematics, using the same approximation of animate links and joints to provide an approximation of the fingertip position. Hence, all inaccuracies in measuring the animate joints, and more so, the inaccuracies in the kinematic model of the animate body, sum to provide, in many cases, an unacceptable approximation of the fingertip. In precision-grasping applications, where small objects are manipulated typically between the thumb and fingertip, and optionally additionally the middle fingertip, such inaccurate fingertip position approximation can cause difficult in the manipulation simulation.

In a preferred embodiment, again where the animate body is the hand, and it is desired to measure the movement of the fingers, the device comprises a link-joint kinematic chain for each finger to be measured. A single reference support is held in position to the dorsal side of the metacarpus. One end of the kinematic chain for each finger is affixed to the reference support. The other end of each kinematic chain is affixed near the tip of each finger. Since each chain accurately measures the position of its respective fingertip relative to the reference support, the fingertip positions are accurately known relative to each other. In contrast to the alternative prior approach where the animate joints, e.g. knuckle of the finger, are measured and forward kinematics used on an approximate model of the fingers to determine the fingertip position, the errors in determining the fingertip positions typically cause the modeled fingertips to be separate from each other in the case were the true fingertips are in contact. Such a case typically occurs with the thumb and index finger, where it is often desired to hold a small object pinched between the thumb and index fingertip and to be able to move the small object while flexing the thumb and index finger and keeping the true fingertips in contact with the object. If only the animate joint angles were measured to determined the fingertip position, errors in the model will typically cause the small object to either be compressed, rotated or even dropped. Thus, the value of accurately measuring the fingertip positions directly with a precise exoskeleton-like device is evident.

For further understanding of the invention, the figures will now be considered. In FIGS. 1A and 1B, a device 100 is depicted mounted on a hand 101, where FIG. 1A is a side view and FIG. 1B is a top view. The finger-measuring device subassembly 102 comprises six links: metacarpal abduction link 103; first, second and third flexure links, 104, 105 and 106, respectively, fingertip strap 108, with the final link being the mating section 119. The flexure link 106 is rotatably mounted on fingertip strap 108 by means of fingertip abduction joint 109. Flexure link 104 is joined to metacarpal abduction link 103 via flexure joint 110 and finger abduction joint 111, thus providing the capability for two orthogonal articulations. Flexure link 104 is joined to flexure link 105 via flexure joint 112, while fluxure link 105 is joined to flexure link 106 via flexure joint 113. Flexure link 104 is shown as having two sections 114 and 115, section 115 fitting into section 114 for telescopic elongation or contraction. Alternatively, a turnbuckle could be used to provide for the length adjustment. Protuberances 116 on section 115 are shown extending through holes in section 114 to lock the sections axially in place.

The hand backplate 117 is shown with two mating sections 118 and 119, which provide for adjustability between finger abduction joint 111 wrist abduction joint 120. The adjustability is accomplished by a portion of the section 118 moving in relation to the mating section 119. As shown, a protuberance 121 is shown as inserted into one of holes 122 to provide a locking registration between the mating sections 118 and 119. Comfortable supporting layers 123 and 124 support the mating sections 118 and 119, respectively, against the hand. The supporting layers should be firm, to hold the mating sections 118 and 119 in position, providing flexibility and damping like a shock absorber. Hand straps 125 and 126 are affixed to mating sections 118 and 119 and hold them against the hand, with the supporting layers 123 and 124 sandwiched in between. For convenience, the straps may be elastic and may be adjusted in any convenient way, such as velcro, snaps, buckles, etc.

A wrist angle measuring structure 127 comprises six links and five joints: wrist abduction links 128 and 129, wrist flexure links 130 and 131, with the final two links being mating section 118 and wriststrap 132; with write flexure joints 134, 135 and 136 and wrist abduction joints 133 and 137. Wriststrap 132 is shown with a rigid portion 138 to which link 132 is affixed. The rigid portion is supported on the wrist with a supporting layer 139. The wriststrap 132 can be adjusted in any convenient way, as described previously for the handstraps.

In FIG. 2 is depicted a device similar to FIG. 1, which comprises two additional device links and joints for measuring the position of a fingertip relative to the metacarpus. These additional links and joints permit the kinematic structure comprising the device links and joints to assume a lower profile when the fingers are extended. A lower profile provides the advantages of lower rotational inertia, a potentially less interfering structure, with reduced probability of hitting other objects, as well as other advantages. The device 200 parallels the components of FIG. 1, where telescoping link 104 is replaced by a structure comprising three non-telescoping links 201, 202 and 203. Links 202 and 203 are joined by joint 204, defining angle 205 between the links, which angle is kept as small as possible to a minimum angle by spring 206. A limit stop depicted as a post 207 prevents angle 205 from passing the minimum angle. Link 201 comprises limit stop 208 to prevent angle 209 from passing a maximum angle. Similarly, link 210 is attached by joint 213 to link 201. Limit stop 211 prevents angle 212 from exceeding a maximum angle. Additionally, link 214 is attached by joint 215 to link 210. Limit stop 216 prevents angle 217 from going below a minimum angle. The stops are positioned to define a set of joint ranges to produce favorable structural profiles as the finger moves. The other elements correspond to the elements in FIG. 1 and are defined accordingly.

In FIGS. 3 to 6 are depicted a number of different embodiments of hinge sensors, which are associated with the joints as depicted in FIGS. 1 and 2. The pin hinges of FIGS. 1 and 2 are merely diagrammatic to depict the joint-link kinematics and the hinge sensors of FIGS. 3 to 6 may be substituted at the various joints, as appropriate for a specific design.

In FIG. 3 a number of related, but different embodiments of hinge sensors are depicted. In the difference embodiments, the sensor is capable of passing through the axis of the joint or generally bows away from the axis of the joint. In FIG. 3A, the sensor is shown passing through the axis of the joint. The hinge 300 has an external yoke 301 and an internal yoke 302 in mating relationship to form an "open" hinge. Pins 303 and 304 connect yokes 301 and 302 and define the rotational axis of the hinge 300. The sensor 305 is rigidly affixed at its ends to the inner surfaces 306 and 307 of yokes 301 and 302, respectively. Links 308 and 309, shown fragmented, extend from yokes 301 and 302, respectively. While the embodiment is depicted with the sensor rigidly affixed to the internal surfaces of the yokes, one or both of the sensor ends can be guided to move relative to the yoke.

Figure 3C:
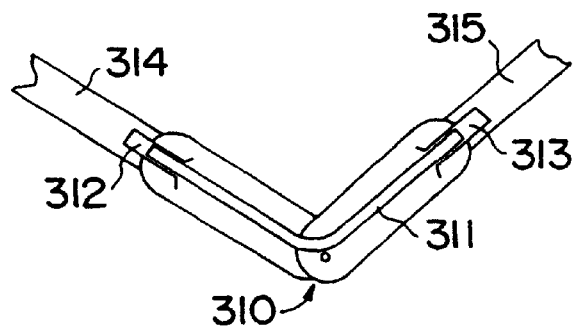

In FIG. 3B is shown a side cross-sectional view of FIG. 3A, showing the hinge 300 with the sensor 305 passing through the hinge axis and having its ends affixed to the yokes. In FIG. 3C is shown a side cross-sectional view, where a hinge 310 comparable to the hinge of FIG. 3A is shown, with sensor 311 having each of its ends in channels 312 and 313, respectively. Channels 312 and 313 extend into links 314 and 315, respectively. With movable ends, the sensor is able to position itself to assume a curve of low resistive force.

Figure 3D:
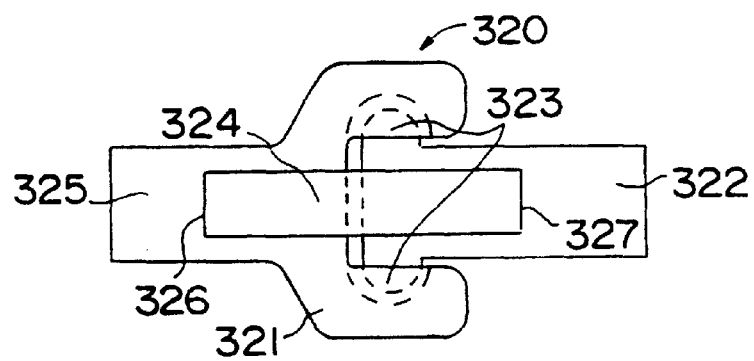
Figure 3E:
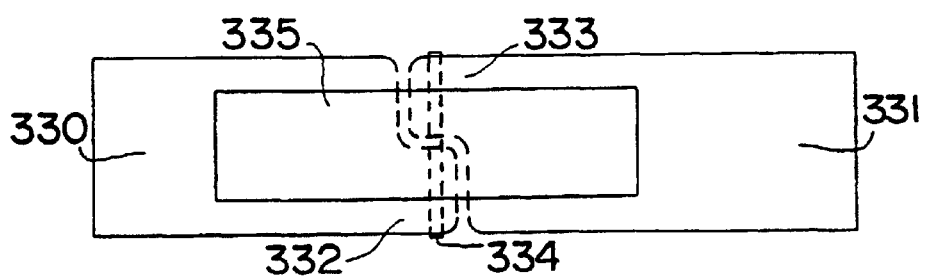

In FIG. 3D is depicted a "closed" hinge 320, formed by external yoke 321, attached to link 325, in conjunction with link 322. Link 322 has protuberances 323 on opposite sides of the link 322, which protuberances extend into concavities in yoke 321, thereby forming a hinge. The sensor 324 is affixed at end 326 to yoke 321 and at end 327 to link 322. An alternate hinge structure is shown in FIG. 3E, where the ends of the links 330 and 331 have mating L-shaped ends 332 and 333, respectively. Pin 334 extends through the L-shaped ends 332 and 333 to define the hinge. The sensor 335 is placed over the links 330 and 331 extending over the pin 334, with the sensor ends affixed to the links 330 and 331, by means such as clips, glue or other convenient fastening means. While the embodiments in FIGS. 3D and 3R are depicted with the sensor rigidly affixed to the internal surfaces of the yokes, one or both of the sensor ends can be guided to move relative to the yoke.

Figure 3F:
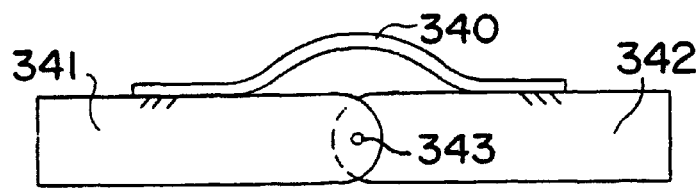
Figure 3G:
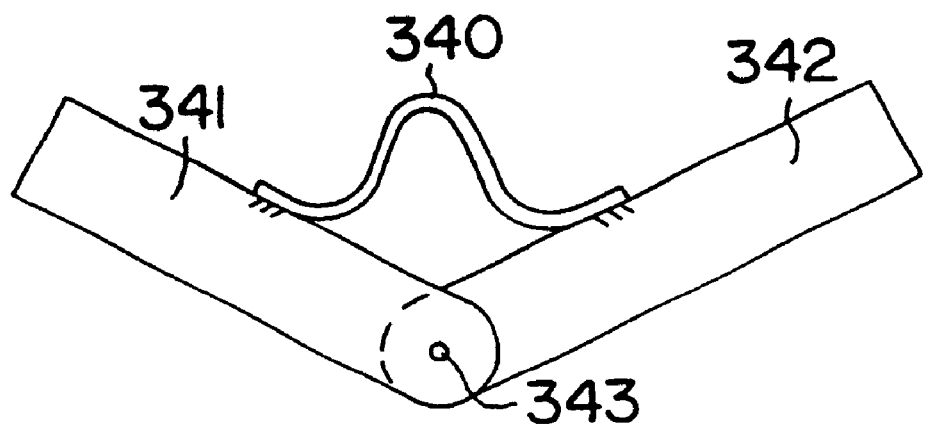
Figure 3H:
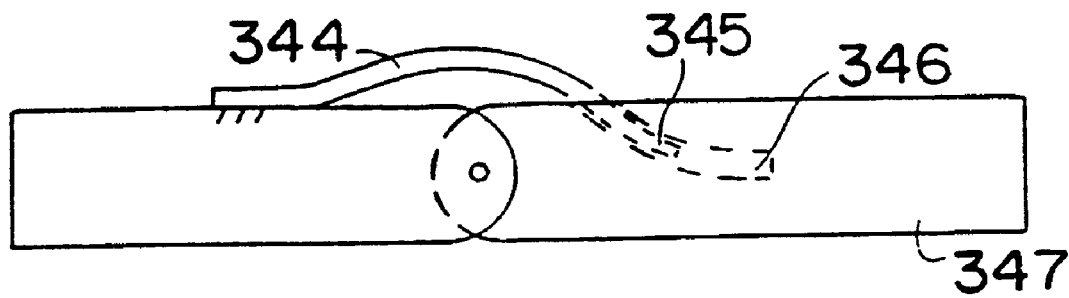
Figure 3I:
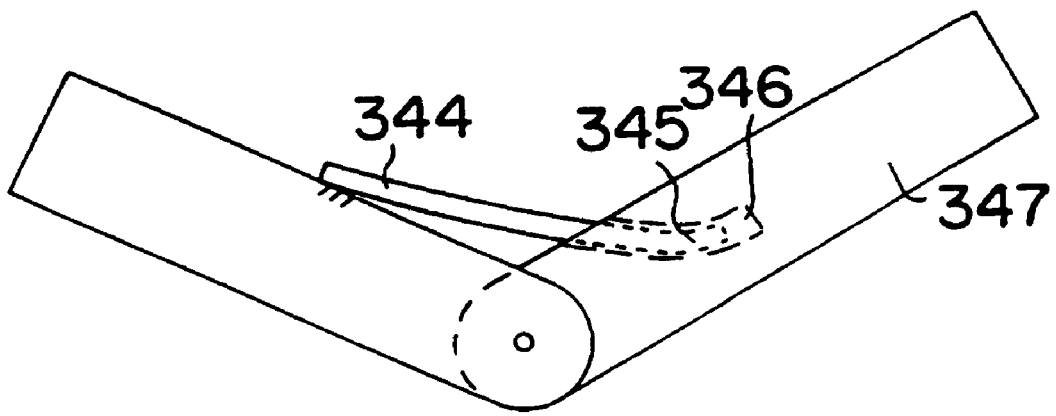

In FIG. 3F, an exemplary cross-section of both FIGS. 3D and 3E is shown, wherein the sensor 340 is shown affixed at its ends to links 341 and 342, to bow around the axis 343. Links 341 and 342 are shown aligned. In FIG. 3G, the links 341 and 342 are shown unaligned, with sensor 340 bowing a greater distance away from axis 343. FIGS. 3H and 3I provide exemplary cross-sections of both FIGS. 3D and 3E, wherein the sensor 344 has at least one of its ends 345 able to slide in a channel 346. Channel 356 extend into link 347. With at least one movable end, the sensor is able to position itself to assume a curve of low resistive force.

Figure 4A:
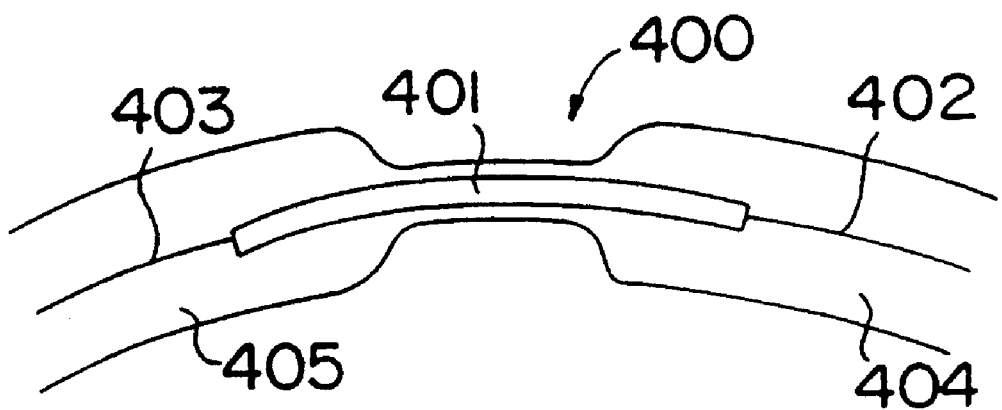
FIGS. 4A and 4B are a side and perspective view, respectively, of a type of sensing device joint employing a variable-resistance strain-sensing goniometer and a flexible hinge.
Figure 4B:
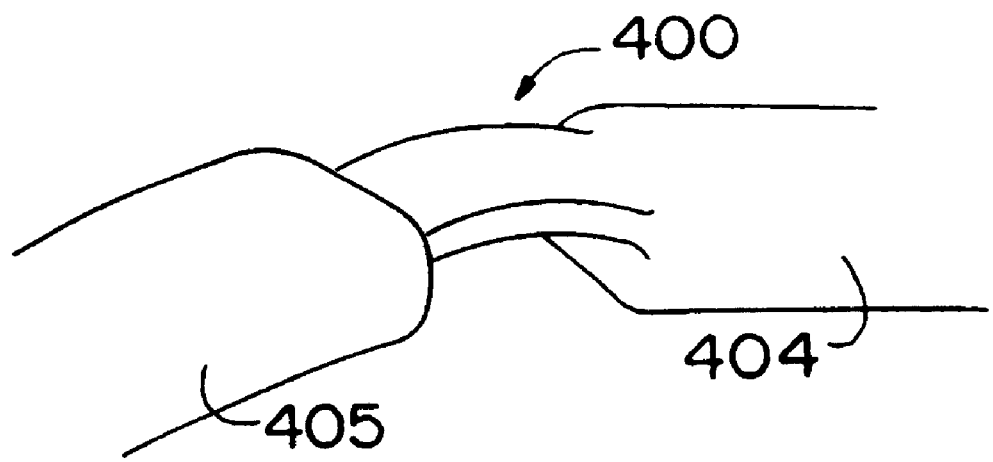

FIG. 4 provides a flex-sensing goniometer 401 (such as the variable strain-sensing goniometers disclosed in U.S. Pat. Nos. 5,047,952 and 5,280,265 by Kramer, et al.) housed in a flexible "living" hinge structure 400. Other flex-sensing goniometer technologies and designs, such as a fiber-optic flex sensor, may also be housed in the living hinge structure. FIG. 4A provides a cross-sectional view while FIG. 4B provides a perspective view. The electrical connections 402 and 403 for the goniometer are incorporated in links 404 and 405. In this embodiment, 402 is the electrical connection to goniometer 401, while 403 is an electrical connection with passes electrically unaltered through goniometer 401 and provides the connection for a second goniometer (not shown) at another portion of link 405. Such electrical connections may take the form of wires, metal traces, conductive polymers, conductive inks, or other such electrically conductive paths. Constructed as such, all goniometers and electrical connections can be housed inside the link-joint structure. The goniometer with its electrical connections can be placed inside the link-joint structure in a variety of ways, including being molded into the structure. Printed circuit techniques, including etching, deposition, and other techniques, which are well known in the electronics industry, may be employed to fabricate such goniometers and their associated electrical connections.

The flex-sensing goniometer may be positioned inside the flexible hinge. Typical hinge materials are plastics and metals which can endure a large number of bend cycles without becoming mechanically damaged. As shown in the cross-section view of FIG. 4A, preferably the goniometer is positioned such that its neutral bend axis is aligned with the neutral bend axis of the flex hinge. The goniometer can lie totally within the hinge material or be only partially covered. The goniometer itself can also be the flex hinge, providing both the angle measurement as well as the material structure of the hinge.

Figure 5A:
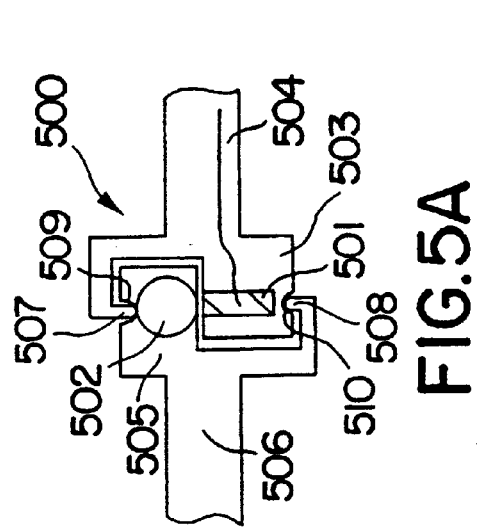
FIGS. 5A and 5B are a side and perspective view, respectively, of a type of sensing device joint employing Hall-Effect sensing technology and pivoting hinges.
Figure 5B:
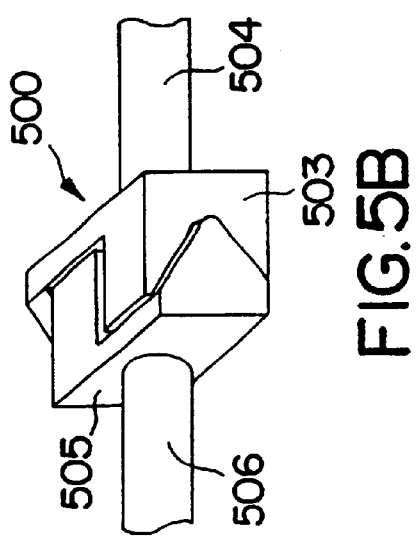

In one embodiment, as shown in FIGS. 5A and 5B, a joint 500 houses a Hall effect goniometer comprising a Hall effect sensor 501 and magnet 502, which goniometer is employed at the joint to measure the angle between links 504 and 506. Other orientations of the sensor and magnet may be employed to improve the structural profile of the sensor, although the depicted embodiment maximizes the range of the sensor. The two mating parts 503 and 505 of the joint are substantially mirror images, each one having a pin, 507 and 508, which sits in a groove, 509 and 510, respectively, defining an axis of joint rotation. The Hall effect sensor 501 is located in the part of the joint 503 at the end of link 504, while the magnet 502 is located in the part 505 at the end of link 506. Such Hall effect goniometers may be employed for measuring the angles at any joint between associated links.

Figure 6A:
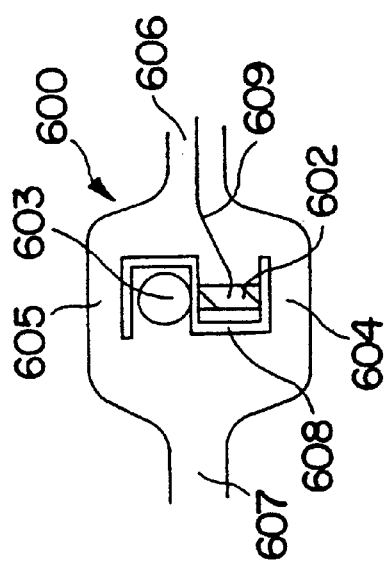
FIGS. 6A and 6B are a side and perspective view, respectively, of a type of sensing device joint employing Hall-Effect sensing technology and flexible hinges.
Figure 6B:
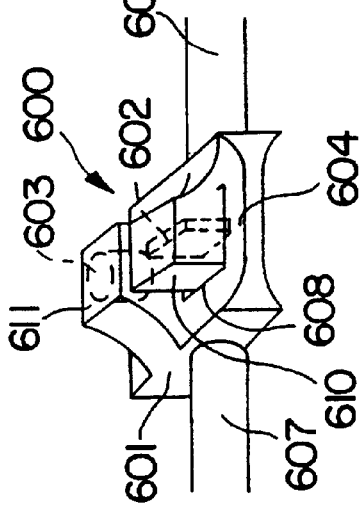

Alternatively, as shown in FIGS. 6A and 6B, a joint 600 with a flexible hinge 601 is used, which can be molded to the appropriate geometry. A Hall effect goniometer comprising sensor 602 and magnet 603 is employed to measure the angle of the joint 600. The Hall effect goniometer components 602 and 603 are positioned to move relative to each other due to the flexibility of regions 604 and 605. Sensor 602 follows the movement of link 606 in fixed alignment. Similarly, magnet 603 follows the movement of link 607 in fixed alignment. Channel 608 separates sensor 602 from magnet 603 and defines the hinge region. The flexible hinge regions 604 and 605 are "living hinges," which define a bend axis as the regions flex. The bend axis is the axis about which the two links articulate. In FIG. 6B is shown a perspective view of joint 600. The appearance of the joint 600 is exemplary of one form and large variations may be made while retaining the function of the joint. Inside the box housing 610 is sensor 602 (shown with broken lines) shown as a rectangularly shaped sensor, while in housing 611 is the magnet (shown with broken lines) shown as a cylindrically shaped magnet.

Figure 7A:
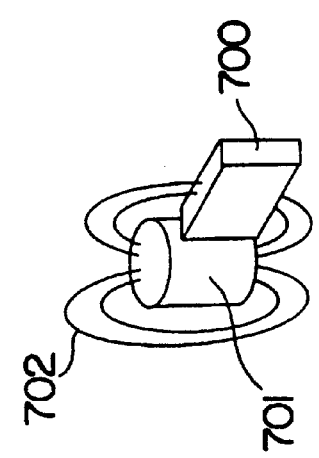
FIGS. 7A and 7B show a Hall-Effect sensor aligned with the magnetic field of a magnet, and at 90 degrees to the field of the magnet, respectively.
Figure 7B:
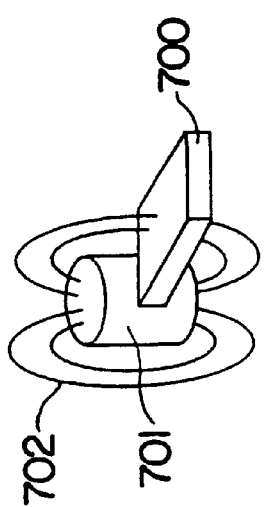

FIG. 7 presents the general operation of a Hall goniometer. In FIGS. 7A and 7B are depicted the extreme positions of the Hall sensor 700. In FIG. 7A, sensor 700 in an aligned configuration with the magnetic field 702 of magnet 701, producing minimum signal. In FIG. 7B, sensor 700 is orthogonal to the magnetic field 702, which provides the maximum signal. The different positions between the extreme positions measure the various angles defined by the links attached to the joint comprising the Hall sensor and magnet.

Figure 8A:
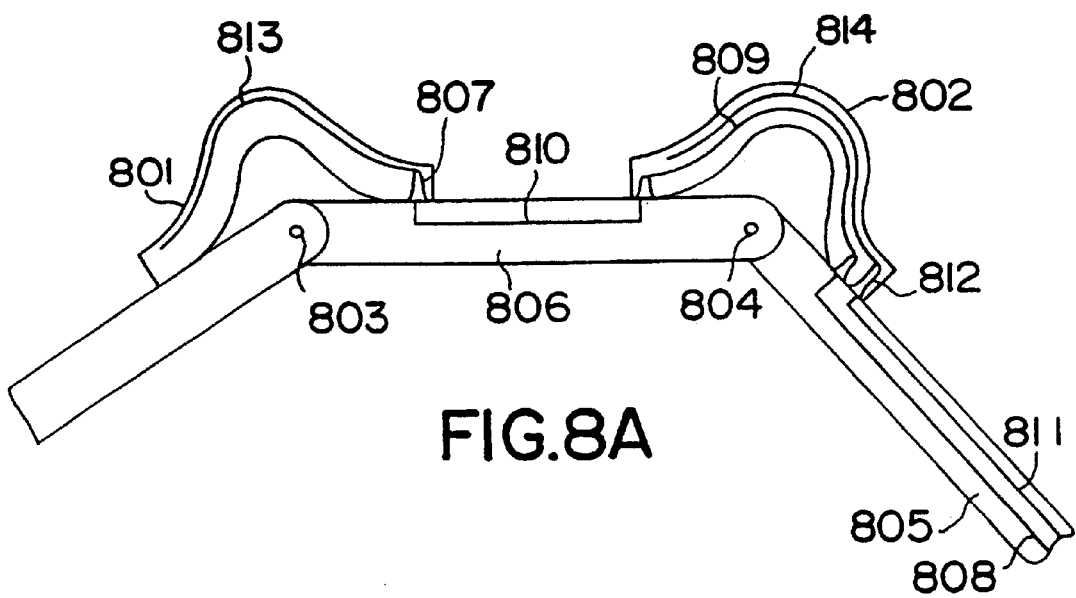
FIGS. 8A and 8B show the side and top view, respectively, of a device structure where the electrical interconnects for the flexible variable-resistance strain-sensing goniometers are part of the device links.
Figure 8B:
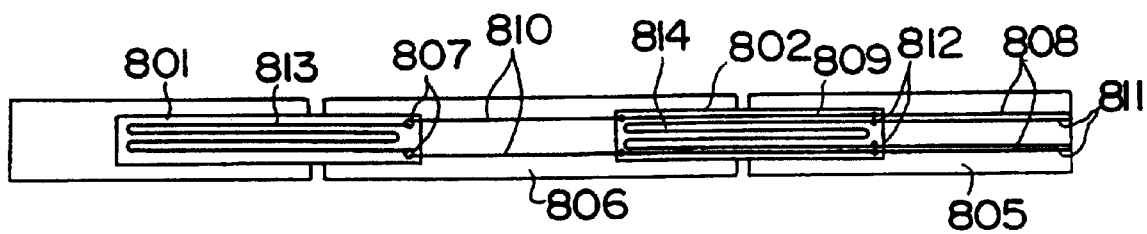

The various hinges depicted in FIGS. 3 and 5 provide that when both ends of the sensors are fixed to the links, it is possible to have the electrodes for the sensors take the form of electrical traces passing through the links. The traces for a distal joint sensor can also pass through the sensor of a joint proximal to one end of the device. This is depicted in FIGS. 8A and 8B. FIG. 8A has flex sensors 801 and 802 straddling joints 803 and 804, respectively. The electrical connections for sensor 801 with sensing grid 813 are incorporated into link 805 as traces 808, the associated non-sensing flex circuit traces 809 pass through the neutral axis of sensor 802, continue into link 806 as traces 810 and terminate at electrodes 807 on sensor 801. Trace 811 is shown to terminate at electrodes 812 on sensor 802 which has sensing grid 814. Although not shown, traces 808 and 811 lead to instrumentation circuitry. FIG. 8B shows a plan view of the device depicted in FIG. 8A with the elements corresponding thereto.

Figure 9:
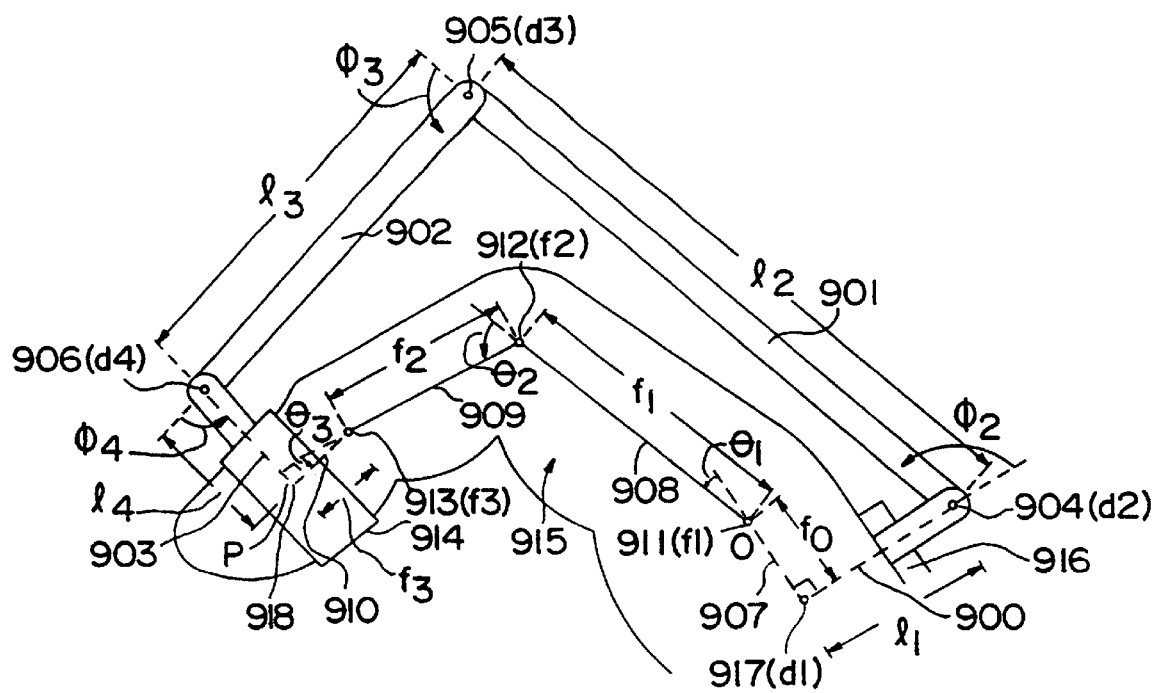
FIG. 9 is the side view of a finger with measurement device attached between the metacarpus and distal phalanx.

FIG. 9 defines the various device and animate links and joints when the animate body is a finger of the hand. The device comprises links 900–903 interconnected by joints 904–906. The animate body, finger 915, comprises animate links 907–910 interconnected by animate joints 911–913. Terminal device link 903 is held firmly in position relative to the terminal animate link 910 by an affixation means 914 which may be a loop, thimble or other such structure. Terminal device link 900 is held firmly in position relative to the terminal animate link 907 by an affixation means 916 which may be a plate or other structure strapped or otherwise held in fixed relation to the metacarpus or other suitable portion near the finger.

To explain the technique for determining animate joint angles, $\theta_1$–$\theta_3$, given sensed device joint angles, $\phi_2$–$\phi_4$, terminology and mathematical techniques, such as those described in *Introduction to Robotics* by John J. Craig, may be used. A 4×4 coordinate transformation from a coordinate frame A to a coordinate frame B is denoted T(A,B). Define P as the point 918, O as the origin 911, s1 and c1 when relating to the device as $\sin(\phi_1)$ and $\cos(\phi_1)$, s1 and c1 when relating to the finger as $\sin(\theta_1)$ and $\cos(\theta_1)$, f0 as the length of finger link O, l1 as device link 1, s123 when relating to the finger as $\sin(\theta_1+\theta_2+\theta_3)$, T(d1,d2) as the coordinate transformation from device coordinate frame 1 to 2, and T(f1,f2) as the coordinate transformation from finger coordinate frame 1 to 2, etc.

Note the following:

For the Device:

$$T(0, d1) = \begin{bmatrix} 0 & 1 & 0 & -f0 \\ -1 & 0 & 0 & 0 \\ 0 & 0 & 1 & 0 \\ 0 & 0 & 0 & 1 \end{bmatrix}$$

$$T(d1, d2) = \begin{bmatrix} c2 & -s2 & 0 & l1 \\ s2 & c2 & 0 & 0 \\ 0 & 0 & 1 & 0 \\ 0 & 0 & 0 & 2 \end{bmatrix}$$

$$T(d2, d3) = \begin{bmatrix} c3 & -s3 & 0 & l4 \\ s3 & c3 & 0 & 0 \\ 0 & 0 & 1 & 0 \\ 0 & 0 & 0 & 1 \end{bmatrix}$$

$$T(d3, d4) = \begin{bmatrix} c4 & -s4 & 0 & l3 \\ s4 & c4 & 0 & 0 \\ 0 & 0 & 1 & 0 \\ 0 & 0 & 0 & 1 \end{bmatrix}$$

$$T(d4, P) = \begin{bmatrix} 0 & 1 & 0 & l4 \\ -1 & 0 & 0 & 0 \\ 0 & 0 & 1 & 0 \\ 0 & 0 & 0 & 1 \end{bmatrix}$$

$$T(P, f3) = \begin{bmatrix} 1 & 0 & 0 & -f3 \\ 0 & 1 & 0 & 0 \\ 0 & 0 & 1 & 0 \\ 0 & 0 & 0 & 1 \end{bmatrix}$$

For the Finger:

$$T(0, f1) = \begin{bmatrix} c1 & -s1 & 0 & 0 \\ s1 & c1 & 0 & 0 \\ 0 & 0 & 1 & 0 \\ 0 & 0 & 0 & 1 \end{bmatrix}$$

$$T(f1, f2) = \begin{bmatrix} c2 & -s2 & 0 & f1 \\ s2 & c2 & 0 & 0 \\ 0 & 0 & 1 & 0 \\ 0 & 0 & 0 & 1 \end{bmatrix}$$

$$T(f2, f3) = \begin{bmatrix} c3 & -s3 & 0 & f2 \\ s3 & c3 & 0 & 0 \\ 0 & 0 & 1 & 0 \\ 0 & 0 & 0 & 1 \end{bmatrix}$$

From the preceding matrices, the transformation from the "origin" coordinate frame 917 to the distal animate joint 913 is calculated by multiplying transformation matrices along the device and along the finger to yield:

Along the Device:

$$\begin{aligned} Td(0, f3) &= T(0, d1)T(d1, d2)T(d2, d3)T(d3, d4)T(d4, P)T(P, f3) \\ &= \begin{bmatrix} -c234 & s234 & 0 & (s234l4 + s23l3 + s2l2 - f0 + c234f3) \\ -s234 & -c234 & 0 & (-c234l4 - c23l3 - c2l2 - l1 + s234f3) \\ 0 & 0 & 1 & 0 \\ 0 & 0 & 0 & 1 \end{bmatrix} \end{aligned}$$

Along the Finger:

$$\begin{aligned} Tf(0, f3) &= T(0, f1)T(f1, f2)T(f2, f3) \\ &= \begin{bmatrix} c123 & -s123 & 0 & (c12f2 + c1f1) \\ s123 & c123 & 0 & (s12f2 + s1f1) \\ 0 & 0 & 1 & 0 \\ 0 & 0 & 0 & 1 \end{bmatrix} \end{aligned}$$

Setting Td(0,f3)=Tf(0,3) and solving yields:

$\theta_1 = a\tan 2(\sin\theta_2,\cos\theta_2)$ $\theta_2 = a\tan 2(y,x) - a\tan 2(f2\sin\theta_2, f1+f2\cos\theta_2)$ $\theta_3 = a\tan 2[-\sin(\phi_2+\phi_3+\phi_4), -\cos(\phi_2+\phi_3+\phi_4)] - \theta_2 - \theta_3$ where:

$x = l4\sin(\theta_2+\theta_3+\theta_4) + l3\sin(\phi_2+\phi_3) + l2\sin\phi_2 - f0 + f3\cos(\phi_2+\phi_3+\phi_4)$ $y = -l4\cos(\phi_2+\phi_3+\phi_4) - l3\cos(\phi_2+\phi_3) - l2\cos\phi_2 - l0 + f3\sin(\phi_2+\phi_3+\phi_4)$ $\cos\theta_2 = (x^2+y^2-f1^2-f2^2)/2f1f2$ $\sin\theta_2 = \pm(1-\cos^2\theta_2)^{-\frac{1}{2}}$ such that the sign + or − is chosen in the expression for $\sin\theta_2$ above to correspond to the non-hyperextended configuration of the finger. The operator atan2 is the arctan function which keeps track of the quadrant of the angle based on the sign of the two operands.

Thus, $\theta1$–$\theta3$ are calculated based on the kinematic models of the finger and device once $\phi2$–$\phi4$ are measured. It is obvious to someone skilled in the art to calculate the position of the finger links and other points on the finger using the calculated angles $\theta1$–$\theta3$, kinematic model and a surface model of the finger.

Figure 10:
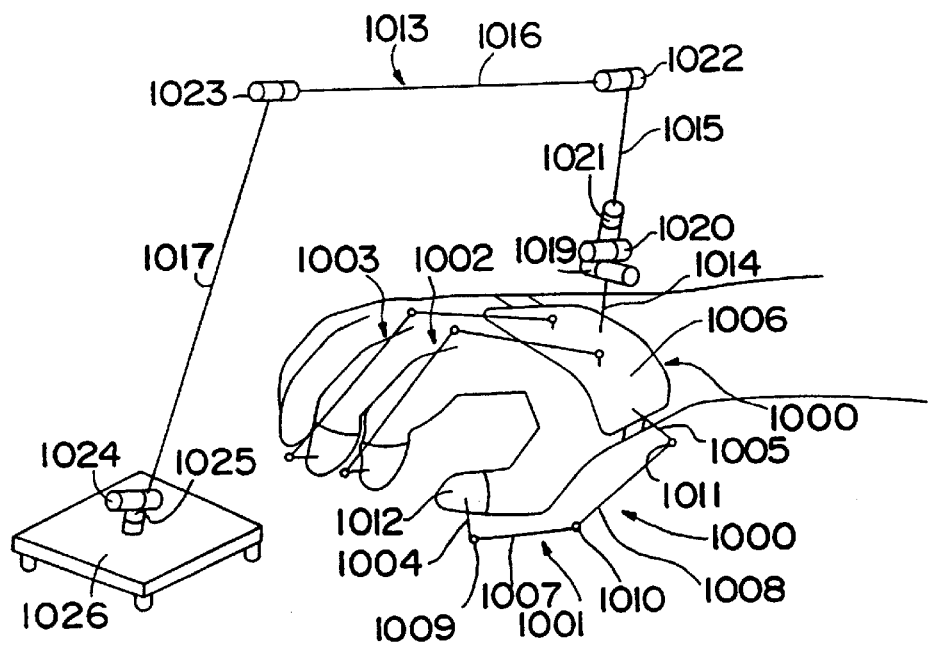
FIG. 10 is a perspective view of a link-joint schematic of a first device for measuring the placement of three finger relative to the back of the hand, and further measuring the placement of the back of the hand relative to a desk-top stand.

FIG. 10 shows a schematic representation of a finger-tracking device for measuring the placement of three fingertips relative to the back of the hand FIG. 10 further shows a schematic joint-link representation of a hand-tracking device for measuring the placement of the back of the hand relative to a fixture 1026 distal to the hand, such as can be placed on a desktop. A device such as shown in FIG. 10 may be used with a similar such device for the other hand. In a useful embodiment, the fixture 1026 for both hands is part of a keyboard or monitor, allowing a user to manipulate and modify graphical objects as presented on their computer monitor. In another embodiment, the device structures of FIG. 10 further comprise vibrotactile and/or force feedback apparatus such that the user can perceive and "feel" computer-simulated objects. The entire device as shown in FIG. 10 can be manufactured to be lightweight and inexpensive, and may be used with consumer and business computer systems.

In FIG. 10, the finger-tracking device 1000 comprises three device kinematic chains 1001, 1002 and 1003, one from each of three fingers, the thumb, index and middle fingers. Device kinematic chains are not shown for the ring and small fingers for clarity, although, they can be included for completeness, or left off for economy. For the thumb, which is exemplary of the other fingers in FIG. 10, the device kinematic chain has one terminal device link 1004 held by an attachment means 1012 to the distal phalanx (animate link) and the other terminal device link 1005 held to a plate 1006 which is secured to the dorsal side of the metacarpus. Also members of the device kinematic chain for the thumb are device links 1007 and 1008. Interconnecting each neighboring pair of the device links 1004, 1005, 1007 and 1008 is a sensing device joint, such as 1009, 1010 and 1011.

The device links are shown schematically as single lines, and the sensing device joints are shown simply as circles. As previously stated, the device links should be rigid enough to transmit angular displacement with a desired accuracy. Typical materials from which the links are made include plastic, metal, composite, wood and the like. Typical sensing device joints may include any appropriate goniometer, such as flexible variable-resistance strain-sensing goniometers, optical encoders, potentiometer, RVDTs, Hall-Effect sensors, resolvers, fiber optic flex sensors and the like. Attachment of a terminal device link to a fingertip may employ a thimble, elastic band, ring, clip, glue, Velcro, strap, cable, string and the like. Similar means may be employed to hold the plate to the back of the palm.

To provide measurement of the entire hand relative to a point separate from the hand, variety of measurement devices and structures may be used. A hand-tracking device providing particular utility is shown in FIG. 10. The hand-tracking device has rigid device links 1014, 1015, 1016, 1017 interconnected by sensing device joints 1019, 1020, 1021, 1022, 1023, 1024 and 1025. The material and sensing specifics of the links and joint of the hand-tracking device may be similar to those of the finger-tracking links and joints. In addition, the hand-tracking device may be replaced with a tracking device based upon electromagnetic ultrasonic, optical tracking sensing technologies, and the like. Fixture 1026 is the location relative to which the placement of the hand is measured. Such a fixture may be stand which conveniently rests on a desktop. There are additional links in FIG. 10 which have not been explicitly mentioned, such as the links between joints 1019 and 1020, joints 1019 and 1020, joints 1020 and 1021, and joints 1024 and 1025. In FIG. 10, these device links are very short in length, and in some cases of zero length.

Figure 11:
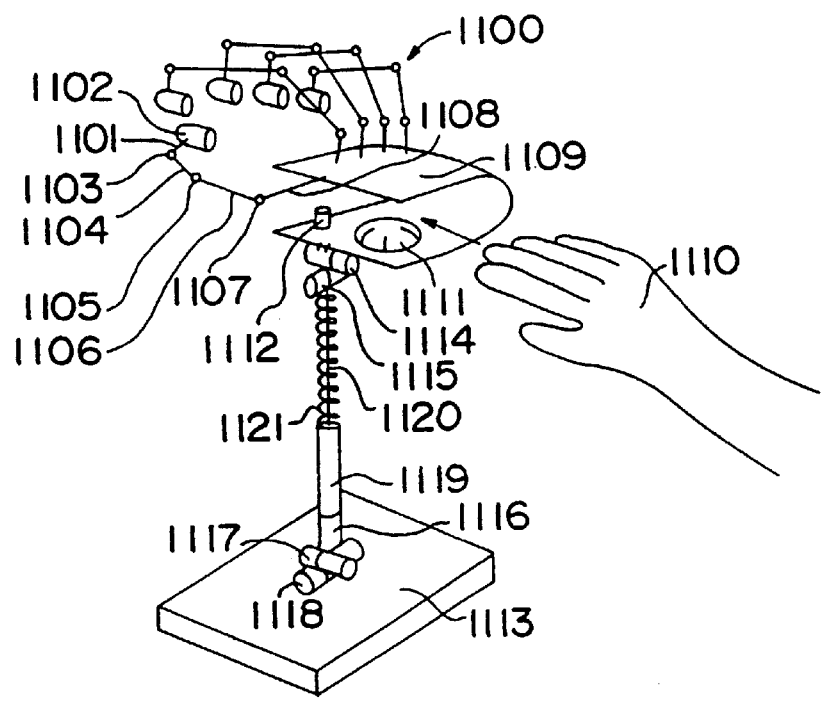
FIG. 11 is a perspective view of a link-joint schematic of a second device for measuring the placement of fingers relative to the back of the hand, and further measuring the placement of the back of the hand relative to a desk-top stand. In this figure, all five fingers are measured.
Figure 12A:
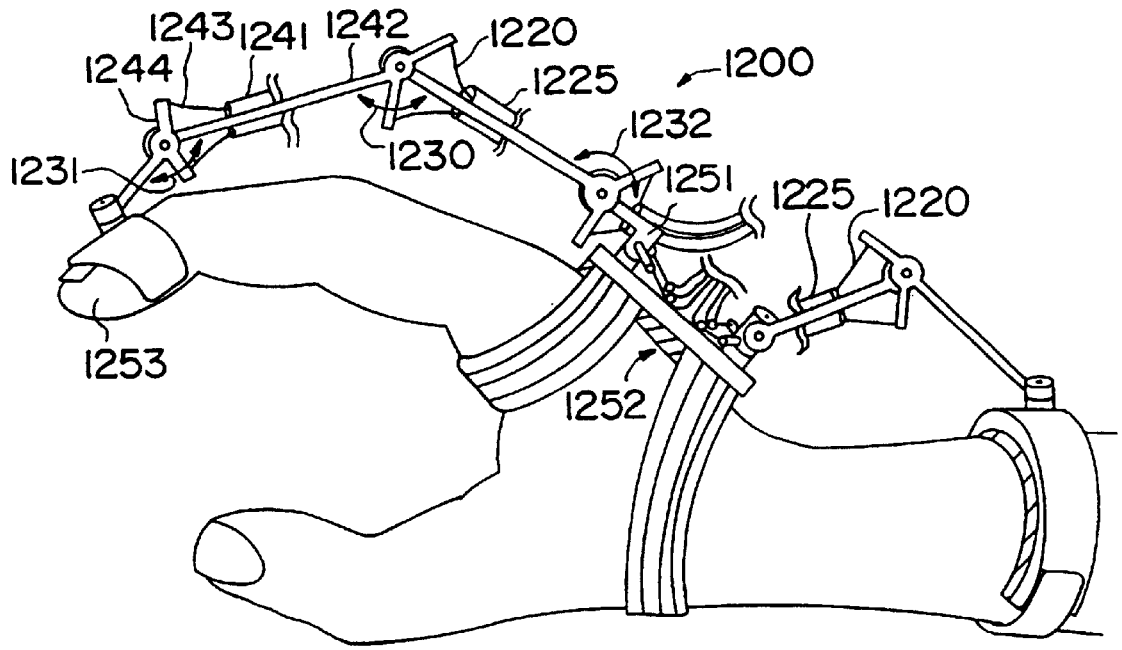
FIG. 12A is a side view of a hand wearing another embodiment of the device in which tendons and sheaths are provided.
Figure 12B:
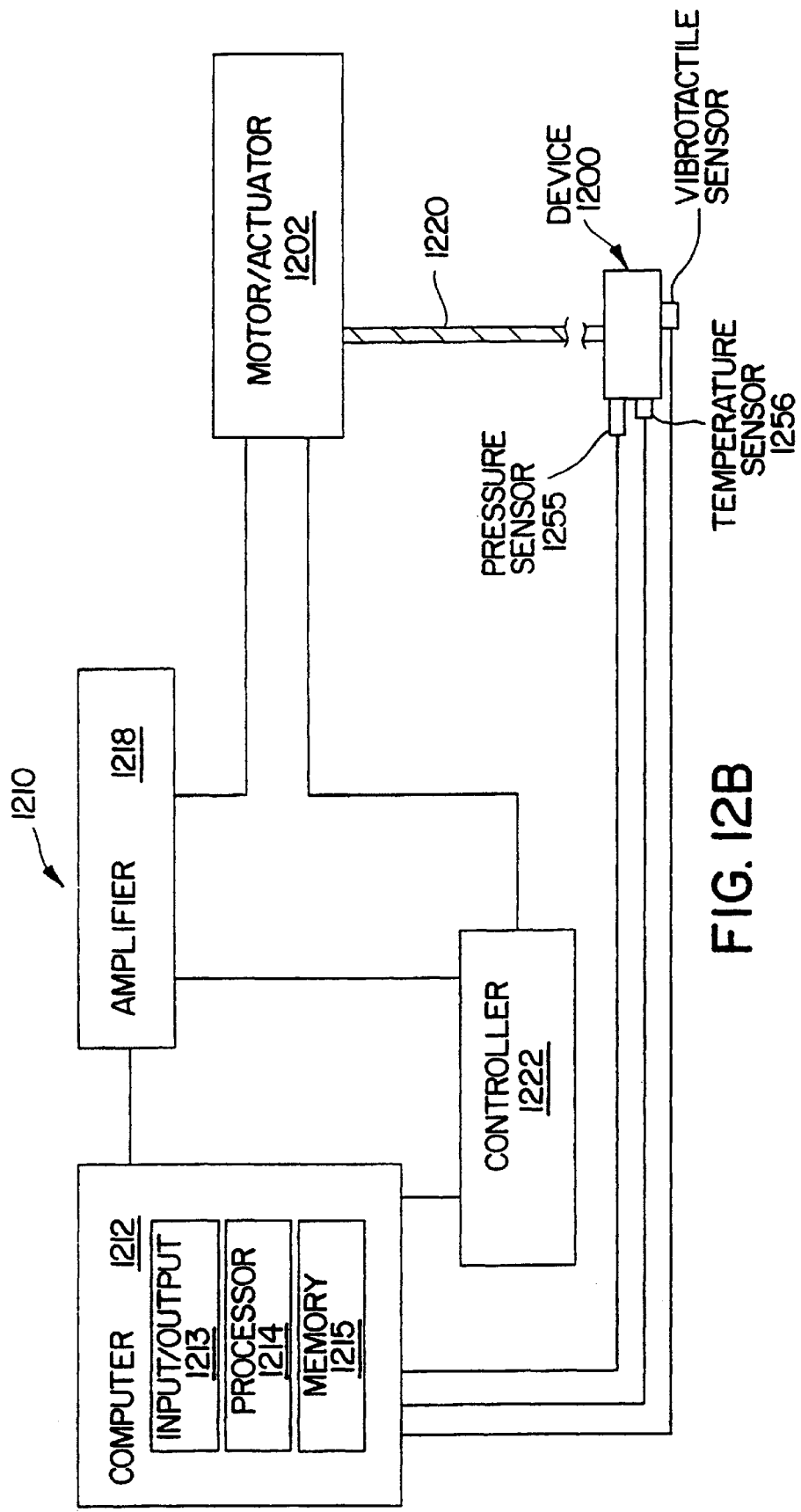
FIG. 12B is a functional diagram showing an exemplary embodiment of force generating means including the computer, controller, amplifier, and rotary motor or linear actuator and the manner in which they interface with the inventive device.
Figure 14:
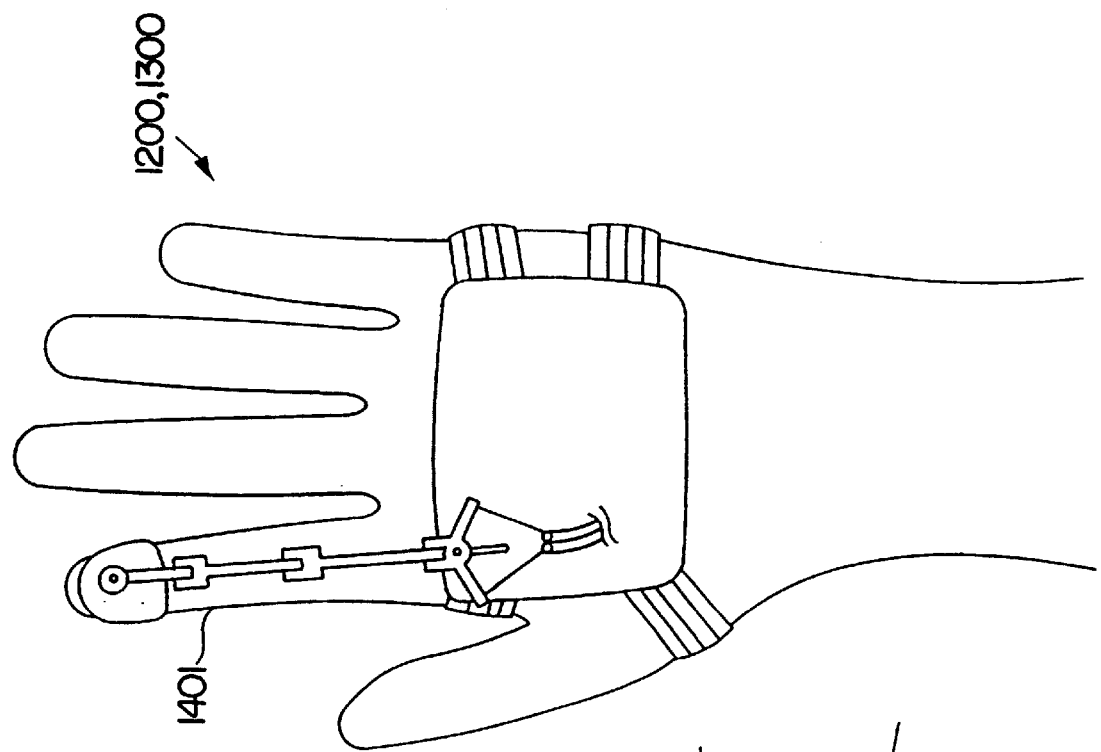
FIG. 14 is a plan view of either of the earlier described embodiments shown in FIGS. 12–13, where force-feedback is employed to cause a finger to abduct or adduct.
Figure 13:
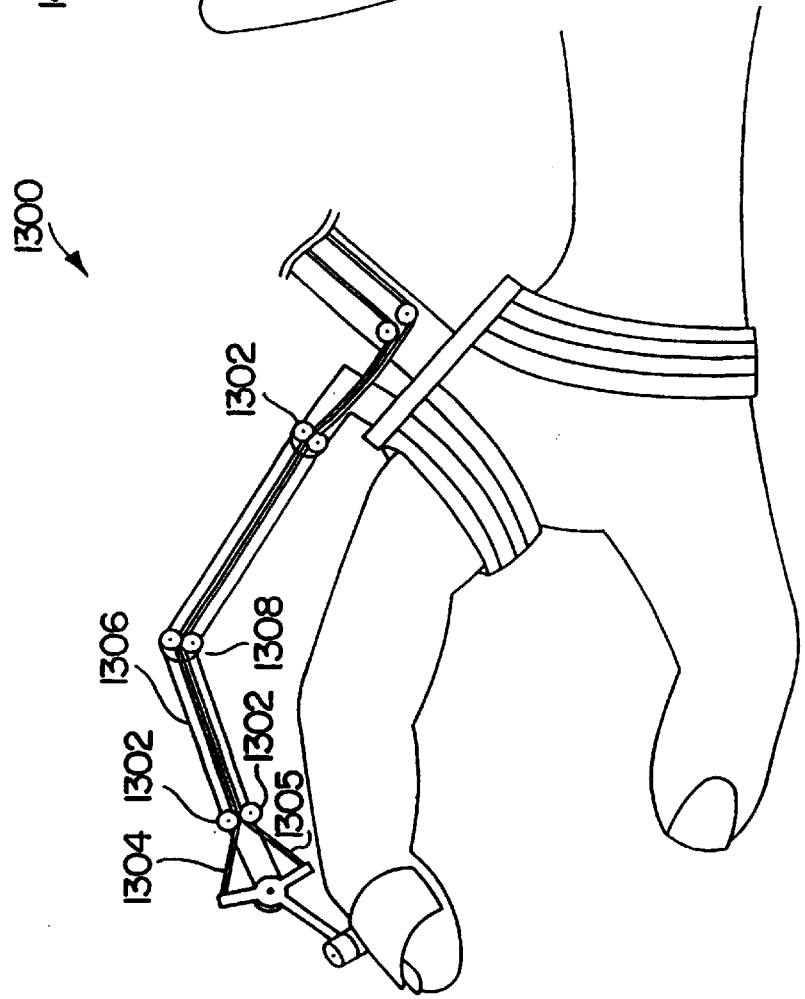
FIG. 13 is a side view of a hand wearing yet another embodiment of the device in which the force-feedback mean utilizes tendons and pulleys to route the tendons.

FIG. 11 shows a five-fingered finger-tracking device 1100 attached to ah and-tracking device of different type than shown schematically in FIG. 10. Similar to FIG. 10, the finger tracking device comprises a set of device kinematic chains, in this case, one chain per finger. For the thumb, which is exemplary of each finger, terminal device link 1101 is held in known relation to the thumbtip by attachment means 1102. Device link 1101 is connected by sensing device joint 1103 to device link 1104, which is connected by sensing device joint 1105 to device link 1106, which is connected by sensing device joint 1107 to device link 1108, which is the terminal device link. Terminal device link 1108 is part of the hand-attachment means, 1109, to which other finger-measurement kinematic chains are terminated.

As shown in FIG. 11, hand-attachment means, 1109, is "C-shaped," and clips onto the palm of hand 1110. Mound 1111 is added to the hand attachment 1109 to provide better support the hand. One or more pegs 1112 may be added to assist with aligning the hand 1110 relative to the hand attachment 1109. Such pegs contact the webbing between the fingers to prevent the hand from sliding too far forward when inserting the hand into the hand attachment. Means other than pegs may be used to accomplish the same desired result.

Hand attachment 1109 is connected to terminal fixture 1113 by a link-joint structure. This structure comprises sensing revolute (rotary) joints 1114–1118 and sensing prismatic (extensory) joint 1119. Prismatic joint 1119 includes sliding link 1120, and optionally supporting spring 1121. As was the case with the embodiment of FIG. 10, the finger- and hand-tracking device of FIG. 11 may include actuation means for providing tactile and/or force reflection to the hand.

The device of FIG. 11 (as is also the case with the device of FIG. 10) finds particular applicability when placed in front of a computer monitor and measurements from the device are used to produce a graphic resemblance of the user's hand on the computer screen, capable of interacting with computer-generated objects. The device may also be used to control a telerobot, or any other device capable of using position information from the hand.

Although the measurement devices disclosed by this application have focused on measurement of the positions of human fingers and hands, other parts of an animate body may be measured using similar techniques, where forward kinematics are used to determine the placement of terminal device links associated with terminal animate links, and where inverse kinematics are used to determine the joint angles of intermediate joints of an animate kinematic chain.

What is claimed is:

1. A method for measuring the relative placement of two animate links separated by at least one animate joint, said method comprising:

providing a device kinematic chain having:
  two terminal device links, each adapted to engage a respective one of the animate links;
  a third device link between said two terminal device links; and
  at least three device joints joined by said terminal device links and said third device link, with at least one of said device joints being displaced away from the animate links in use, at least two of said device joints being sensing joints on opposing ends of said third device link, wherein the number of said sensing joints is at least sufficient to determine the relative placement of the two animate links;
measuring the angle of each of said sensing joints;
transmitting the angle measurement for each of said sensing joints as an electrical signal to a signal processor; and
determining the relative placement of the two animate links from said electrical signals.

2. A method according to claim 1, comprising determining the relative placement of the two animate links using inverse kinematics of the animate links and the at least one animate joint.

3. A method according to claim 1, wherein the two animate links are separated by at least one intermediate animate link, and further comprising determining the relative placement of the at least one intermediate animate link using inverse kinematics on the animate links and the at least one animate joint.

4. A method according to claim 1, comprising determining the relative placement of the two animate links by:
  calculating the relative placement of said two terminal device links from said electrical signals; and
  calculating at least one animate joint angle using the relative placement of said two terminal device links.

5. A method according to claim 1, wherein said determining considers the placement of a device link on an animate link.

6. A method according to claim 1, wherein said device kinematic chain comprises at least three sensing joints.

7. A method according to claim 1, wherein said device kinematic chain comprises at least four device joints.

8. A method according to claim 7, wherein the axes of at least three device joints are parallel.

9. A method according to claim 1, further comprising measuring the placement of a third animate link.

10. A method for measuring the relative placement of two terminal animate links separated by at least one animate joint, the method comprising:
  providing a device kinematic chain having:
    two terminal device links, each adapted to engage a respective one of the terminal animate links;
    an intermediate device link; and
    at least three device joints joined by said intermediate device link and said terminal device links, with at least one device joint being displaced away from the terminal animate links in use, at least two of said device joints being sensing joints attached at opposing ends of said intermediate device link, and at least one of said device joints being a non-sensing joint, wherein the number of said sensing joints is at least sufficient to determine the relative placement of the two terminal animate links;
  measuring the angle of each of said sensing joints;
  transmitting the angle measurement for each of said sensing joints as an electrical signal to a signal processor; and
  determining the relative placement of the two animate links from said electrical signals.

11. A method for measuring the relative placement of two animate links separated by at least one animate joint, the method comprising:
  providing a device kinematic chain having three sensing joints joining four device links, two of said four device links being adapted to engage a respective one of the animate links;
  measuring the angle of each of said sensing joints;
  transmitting the angle measurement for each of said sensing joints as an electrical signal to a signal processor; and
  determining the relative placement of the two animate links from said electrical signals.

12. A method according to claim 11, wherein the two animate links are separated by at least one intermediate animate link, and further comprising determining the relative placement of the at least one intermediate animate link using inverse kinematics on the animate links and the at least one animate joint.

13. A method for measuring the relative placement of two animate links separated by at least one animate joint, the method comprising:
  providing a device kinematic chain having:
    two terminal device links, each adapted to engage a respective one of the animate links;
    intermediate device links; and
    at least four device joints having parallel axes and joined by said intermediate device links and said terminal device links, with at least one device joint displaced from the surface of the animate links, at least two of said device joints being sensing device joints attached to opposing ends of an intermediate device link, the number of device joints which are sensing device joints being at least sufficient to determine the relative placement of the two animate links;
  measuring the angle of each of said sensing device joints;
  transmitting the angle measurement for each of said sensing device joints as an electrical signal to a signal processor; and
  determining the relative placement of the two animate links from said electrical signals.

14. A method for measuring the relative placement of two terminal animate links separated by at least two animate joints of at least one animate kinematic chain, the animate kinematic chain comprising a portion of a hand including at least a portion of a finger, said method comprising:
  employing a device kinematic chain having terminal device links, each engaging a terminal animate link, and intermediate device links, said device kinematic chain comprising a plurality of device joints with at least one device joint displaced away from said animate links and said device joints being joined by said terminal device links and said intermediate device links, where the number of device joints is at least three comprising at least two sensing device joints on opposite ends of an intermediate device link, where the number of sensing device joints is sufficient to determine the relative placement of said two terminal animate links;
  measuring the angle of each of said sensing device joints;
  transmitting the angle measurement for each of said sensing device joints as an electrical signal to a signal processor; and determining the relative placement of the two terminal animate links of the portion of the hand from said electrical signals.

15. A method according to claim 14, wherein the terminal animate links are the distal phalanx of the finger and the metacarpus of the hand.

16. A method according to claim 14, wherein said method comprises measuring a plurality of the animate kinematic chains.

17. A device for measuring the relative placement of two animate links separated by at least one animate joint, said device comprising:
- at least one device kinematic chain comprising:
  - at least three device joints comprising at least two sensing joints, said sensing joints outputting electrical signals related to the angle of said sensing device joint; and
  - at least two device links including two device links each capable of engaging a respective animate link, said device links joining said device joints, wherein two sensing joints are attached on opposite ends of a device link;
- a signal transmission means for transmitting said electrical signals; and
- a signal processor receiving said electrical signals and determining the relative placement of the two animate links.

18. A device according to claim 17, wherein said device comprises at least two device kinematic chains.

19. A device according to claim 18, wherein two of said kinematic chains share a common link.

20. A device according to claim 17, wherein said device kinematic chain comprises at least three sensing joints.

21. A device according to claim 17, wherein said device kinematic chain comprises at least four device joints.

22. A device according to claim 21, wherein the axes of at least three device joints are parallel.

23. A method according to claim 1, wherein said device links are each affixed to an animate link by an attachment.

24. A method according to claim 10, wherein said device links are each affixed to an animate link by an attachment.

25. A method according to claim 11, wherein said device links are each affixed to an animate link by an attachment.

26. A method according to claim 11, wherein said four device links include the terminal device links.

27. A method according to claim 13, wherein said device links are each affixed to an animate link by an attachment.

28. A method according to claim 14, wherein said terminal device links are each affixed to a terminal animate link by an attachment.

29. A device according to claim 17, further comprising two attaching means for individual attachment to the two animate links.

30. A device according to claim 29 wherein said device links are capable of engaging the animate links through the attaching means.

31. A device according to claim 17 further comprising at least one intermediate device link between said device links.

32. A method for measuring the relative placement of two animate links separated by at least one animate joint, said method comprising:
- providing a device kinematic chain having:
  - intermediate device links and two terminal device links, each of said terminal device links adapted to engage a respective one of the animate links; and
  - at least three sensing device joints, joined by said intermediate device links and said terminal device links;
- measuring the angle of each of said sensing device joints;
- transmitting the angle measurement for each of said sensing device joints as an electrical signal to a signal processor; and
- determining the relative placement of the two animate links from said electrical signals.

33. A method according to claim 32, wherein said device links are each affixed to an animate link by an attachment.

34. A device for measuring the relative placement of two animate links separated by at least one animate joint, said device comprising:
- at least one device kinematic chain comprising:
  - intermediate device links;
  - at least three sensing device joints joined by said intermediate device links, said sensing device joint producing electrical signals related to the angle of said sensing device joint; and
  - two terminal device links each capable of engaging a respective animate link, said terminal device links joined to a respective one of two of said sensing joints;
- a signal transmission means for transmitting said electrical signals; and
- a signal processing means receiving said electrical signals to determine the relative placement of the two animate links.

35. A device according to claim 34, wherein the device kinematic chain comprises at least four device joints.

36. A device according to claim 34, wherein two sensing device joints are on opposing ends of one of said intermediate device links.

* * * * *